United States Patent

Tice et al.

[11] Patent Number: 6,107,485
[45] Date of Patent: Aug. 22, 2000

[54] HIGH PRESSURE PROCESS TO PRODUCE 2-ARYL-3-SUBSTITUTED PYRIMIDIONE HERBICIDES

[75] Inventors: Colin Michael Tice, Elkins Park; Zev Lidert, Doylestown, both of Pa.

[73] Assignee: Rohm and Haas Company, Phila., Pa.

[21] Appl. No.: 09/467,867

[22] Filed: Dec. 20, 1999

Related U.S. Application Data

[60] Provisional application No. 60/113,206, Dec. 22, 1998.

[51] Int. Cl.$^7$ .................................................. C07D 239/36

[52] U.S. Cl. ............................................................ 544/319

[58] Field of Search ............................................ 544/319

[56] References Cited

U.S. PATENT DOCUMENTS

| | | | |
|---|---|---|---|
| 5,300,477 | 4/1994 | Tice | 504/242 |
| 5,453,414 | 9/1995 | Tice | 504/133 |
| 5,726,124 | 3/1998 | Tice | 504/193 |

*Primary Examiner*—John M. Ford
*Attorney, Agent, or Firm*—Clark R. Carpenter

[57] ABSTRACT

This invention describes a new and convenient single step process for preparing 2-aryl-3-substituted-4(3H)-pyrimidinone herbicides by reacting a N-substituted amidine (or its hydrohalide salt) with a β-keto ester under conditions of high pressure. The 2-aryl-3-substituted pyrimidinone compounds produced by the process of the present invention are very useful as herbicidal agents for the control of weeds in agronomically important crops.

11 Claims, No Drawings

HIGH PRESSURE PROCESS TO PRODUCE 2-ARYL-3-SUBSTITUTED PYRIMIDIONE HERBICIDES

This is a non-provisional application of prior pending provisional application Ser. No. 60/113,206 filed Dec. 22, 1998.

This invention relates to a new and convenient single step process for preparing 2-aryl-3-substituted-4(3H)-pyrimidinone herbicides by reacting a N-substituted amidine (or its hydrohalide salt) with a β-keto ester. The 2-aryl-3-substituted pyrimidinone compounds produced by the process of the present invention are very useful as herbicidal agents for the control of weeds in agronomically important crops. Such uses are disclosed in both U.S. Pat. No. 5,300,477, U.S. Pat. No. 5,453,414 and U.S. Pat. No. 5,726,124.

Direct reaction of N-substituted amidines (Formula II, $R^3 \neq H$) with β-keto esters (Formula III, $R^6$=alkyl) which are monosubstituted at the α-position does not give useful yields of 2-aryl-3-substituted pyrimidinones (Formula I, $R^3 \neq H$, $R^6$=alkyl) under normal conditions.

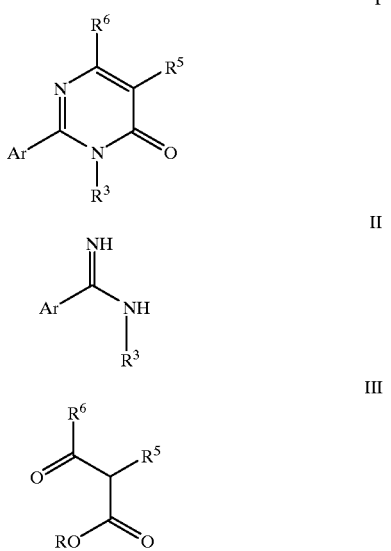

Existing art for preparation of a 2-aryl 3-substituted pyrimidinone herbicides requires alkylation, for example propargylation, of an intermediate 2-aryl-3-unsubstituted pyrimidinone (Formula I, $R^3$=H) and gives a mixture of N- and O-alkylation products that are difficult to separate. Often the undesired O-alkylated product predominates. Thus, the single step process of the present invention represents a distinct advantage over the prior work for preparing such 2-aryl-3-substituted pyrimidinone herbicides.

The processes disclosed in U.S. Pat. Nos. 5,300,477, 5,453,414, 5,726,124 and EP 0 812 832 A (published Dec. 17, 1997) neither disclose nor suggest the process of the present invention. A. Sitte et al., *Chem. Ber.* 102, 615–622 (1969) discloses that N-monoalkylated benzamidines, which are related to the N-substituted amidines used in the present invention, do not react with a-monoalkylated β-ketoesters, which are similar to the β-keto esters used in the present invention, to form the 2-aryl-3-substituted pyrimidinones of the present invention under conditions that work for N-monoalkylated benzamidines with unsubstituted acetoacetic esters. I. Huber et al., *J. Chem. Soc. Perkin Trans* 1, 1987, 909–912 describe the successful preparation of fused tricyclic pyrimidinones by reaction between N-monoalkylated cyclic amidines and cyclic β-ketoesters. Again, the process of the present invention is neither disclosed nor suggested.

In summary, this invention provides a process for the preparation of a 2-aryl-3-substituted-4(3H)-pyrimidinone of formula (I) by reacting a N-substituted amidine or its hydrochloride salt of formula (II) with a β-keto ester of formula (III) in the presence of a base and a solvent using high pressure

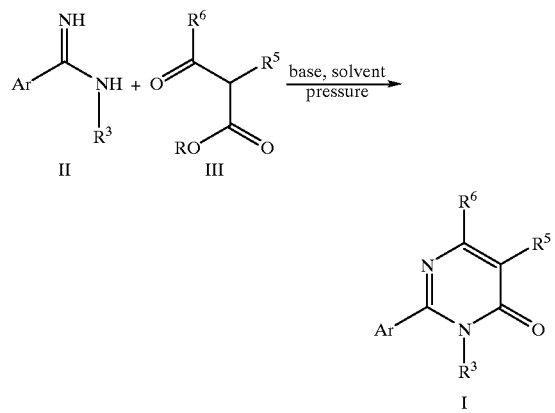

wherein

Ar is furyl, naphthyl, phenyl, pyridyl or thienyl; or furyl, naphthyl, phenyl, pyridyl or thienyl substituted with up to three substituents independently selected from bromo, chloro, fluoro, $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, halo$(C_2-C_{12})$alkenyl, halo$(C_2-C_{12})$alkynyl, $(C_1-C_{12})$alkoxy, $(C_1-C_{12})$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_{12})$alkoxy, 1,3-dioxalan-2-yl and nitro; or furyl, naphthyl, phenyl, pyridyl or thienyl substituted on two adjacent carbon atoms by an alkylenedioxy to form a fused heterocyclic ring containing two oxygen atoms;

$R^3$ is $(C_1-C_6)$alkyl, $(C_3-C_6)$alkenyl, $(C_3-C_6)$alkynyl, $(C_1-C_6)$alkoxy$(C_2-C_6)$alkyl, methyl or $C_3$ alkynyl substituted with up to three halo, or $(C_2-C_6)$alkyl, $(C_3-C_6)$alkenyl, $(C_4-C_6)$alkynyl or $(C_1-C_6)$alkoxy$(C_2-C_6)$alkyl all substituted with up to five halo;

$R^5$ is $(C_1-C_6)$alkyl, $(C_1-C_6)$alkoxy, halo$(C_1-C_6)$alkyl, halo$(C_1-C_6)$alkoxy or $(C_1-C_6)$alkylthio;

$R^6$ is $(C_1-C_{12})$alkyl or cyclo$(C_3-C_7)$alkyl; and

R is $(C_1-C_{12})$alkyl.

In a preferred embodiment of this invention,

Ar is furyl, naphthyl, phenyl, 3,4-methylenedioxyphenyl, pyridyl, thienyl, or furyl, naphthyl, phenyl, pyridyl or thienyl substituted with up to three substituents independently selected from bromo, chloro, fluoro, $(C_1-C_6)$alkyl, cyclo$(C_5-C_6)$alkyl, $(C_2-C_6)$alkenyl, cyclo$(C_5-C_6)$alkenyl, $(C_2-C_6)$alkynyl, halo$(C_1-C_6)$alkyl, halo$(C_2-C_6)$alkenyl, halo$(C_2-C_6)$alkynyl, $(C_1-C_6)$alkoxy, $(C_1-C_6)$alkylthio, $(C_1-C_6)$alkylsulfonyl, $(C_1-C_6)$alkylsulfinyl, phenyl, phen$(C_1-C_6)$alkyl, phen$(C_2-C_6)$alkenyl, phen$(C_2-C_6)$alkynyl, cyano, halo$(C_1-C_6)$alkoxy, 1,3-dioxalan-2-yl and nitro;

$R^3$ is methyl, ethyl, n-propyl, $(C_3-C_4)$alkenyl, $(C_3-C_6)$alk-2-ynyl, $(C_1-C_2)$alkoxy$(C_2-C_3)$alkyl, or methyl, ethyl, n-propyl, $(C_3-C_4)$alkenyl, $(C_3-C_6)$alk-2-ynyl, $(C_1-C_2)$alkoxy$(C_2-C_3)$alkyl substituted with one or more halo;

$R^5$ is methyl, ethyl, n-propyl, isopropyl, halo($C_1$–$C_2$) alkyl, halo($C_1$–$C_2$)alkoxy, ($C_1$–$C_2$)alkoxy or ($C_1$–$C_2$) alkylthio;

$R^6$ is methyl, ethyl, n-propyl, n-butyl, n-pentyl, n-hexyl, sec-butyl, isopropyl, isobutyl, cyclopropyl, cyclobutyl or cyclopentyl; and R is ($C_1$–$C_6$)alkyl.

In a more preferred embodiment of this invention,

Ar is 2-furyl, 3-furyl, 4-chloro-2-furyl, 5-chloro-2-furyl, 5-chloro-3-furyl, 2,5-dichloro-3-furyl, 2-naphthyl, phenyl, 3-methylphenyl, 3-methoxyphenyl, 3-nitrophenyl, 4-fluorophenyl, 4-chlorophenyl, 3-trifluoromethylphenyl, 3-bromophenyl, 3-chlorophenyl, 3-fluorophenyl, 3-trifluoromethoxyphenyl, 3-cyanophenyl, 3-(1,3-dioxolan-2-yl)phenyl, 2-fluorophenyl, 2-chlorophenyl, 2-trifluoromethoxyphenyl, 3,5-difluorophenyl, 3,5-dichlorophenyl, 2,4-difluorophenyl, 2,5-difluorophenyl, 3-chloro-4-fluorophenyl, 3,4-difluorophenyl, 3-fluoro-5-trifluoromethylphenyl, 3,4,5-trifluorophenyl, 3,4-methylenedioxyphenyl, 2-pyridyl, 4-chloro-2-pyridyl, 6-chloro-2-pyridyl, 4,6-dichloro-2-pyridyl, 3-pyridyl, 5-bromo-3-pyridyl, 5,6-dichloro-3-pyridyl, 5-chloro-3-pyridyl, 5-fluoro-3-pyridyl, 4-pyridyl, 2-fluoro-4-pyridyl, 2-chloro-4-pyridyl, 2-chloro-6-methyl-4-pyridyl, 2-methyl-4-pyridyl, 2-methoxy-4-pyridyl, 2-cyano-4-pyridyl, 2,6-difluoro-4-pyridyl, 2,6-dichloro-4-pyridyl, 2-thienyl, 3-thienyl, 4-chloro-2-thienyl, 5-chloro-2-thienyl, 5-chloro-3-thienyl or 2,5-dichloro-3-thienyl;

$R^3$ is ethyl, allyl, 3-chloroallyl, prop-2-ynyl, but-2-ynyl, pent-2-ynyl or 2-methoxyethyl;

$R^5$ is methyl, ethyl, halo($C_1$–$C_2$)alkyl, difluoromethoxy, trifluoromethoxy, methoxy or methylthio;

$R^6$ is methyl, ethyl, n-propyl, sec-butyl, isopropyl, isobutyl, cyclopropyl, cyclobutyl or cyclopentyl; and R is ($C_1$–$C_4$)alkyl.

In an even more preferred embodiment of this invention,

Ar is phenyl, 3-fluorophenyl, 3-chlorophenyl, 3,5-difluorophenyl, 3,5-dichlorophenyl, 3-chloro-4-fluorophenyl, 5-chloro-3-pyridyl, 2-chloro-4-pyridyl, 2,6-dichloro-4-pyridyl or 2-fluoro-4-pyridyl;

$R^3$ is prop-2-ynyl;

$R^5$ is methyl, ethyl or methoxy;

$R^6$ is methyl or ethyl, and

R is methyl or ethyl.

In a most preferred embodiment of this invention, Ar is phenyl or 2,6-dichloro-4-pyridyl.

The groups such as alkyl, alkenyl, alkynyl, alkoxy, alkylthio and the like as well as other moieties containing these groups, such as aralkyl, alkoxyalkyl, alkylsulfonyl and the like, described hereinabove and below can be either a straight chain such as n-propyl or a branched chain such as isobutyl or tert-butyl. The prefix halo in such groups, such as haloalkyl, haloalkoxy and the like, can represent monohalo, polyhalo in which the halogen atoms can be the same or different, or perhalo.

Alkylenedioxy represents an alkylene group which is appended by an oxygen at each terminal carbon atom, for example oxymethyleneoxy (—O—$CH_2$—O—) or oxyethyleneoxy (—O—$CH_2CH_2$—O—).

The reaction between II (or II.hydrohalide salt) and III is run in an alcohol solvent, preferably methanol or ethanol at a temperature of 0–100° C., preferably 15–35° C. for a period of 1h to 10 days, preferably 0.5–4 days. Preferably the solvent is anhydrous. Between 1 and 10 equivalents of a tertiary amine base such as triethylamine, diisopropylethylamine, pyridine or lutidine is added to the reaction mixture. A preferred tertiary amine base is triethylamine. The reaction is run under a pressure of 6–20 Kbar, preferably 10–20 Kbar.

The following example is provided for additional guidance to the practitioner of this invention.

Preparation of 2-(2,6-dichloro-4-pyridyl)-5-methoxy-6-ethyl-3-propargyl-4(3H)-pyrimidinone A solution of 2,6-dichloropyridine-4-(N-propargyl) carboxamidine hydrochloride (15 g, 51 mmol), methyl 2-methoxy-3-oxopentanoate (12 g, 76 mmol, 1.5 eq) and triethylamine (10 mL, 72 mmol) in 90 mL of ethanol was placed in a Teflon® ampoule and subjected to a piston cylinder high-pressure apparatus and compressed at a pressure of 10 kbar at room temperature for 3 days. The mixture was concentrated under reduced pressure, diluted with ether, washed with 5% aqueous hydrochloric acid and saturated aqueous sodium bicarbonate, and dried over magnesium sulfate. The solvent was removed under reduced pressure and the crude product was purified by flash chromatography on silica gel eluting with a gradient of 10% to 60% ethyl acetate in hexanes to afford 5.1 g (30%) of 2-(2,6-dichloro-4-pyridyl)-5-methoxy-6-ethyl-3-propargyl-4(3H)-pyrimidinone as a white solid, mp 112–115° C.

We claim:

1. A process for the preparation of a 2-aryl-3-substituted-4(3H)-pyrimidinone of formula (I) by reacting a N-substituted amidine or its hydrochloride salt of formula (II) with a β-keto ester of formula (III) in the presence of a base and a solvent using high pressure

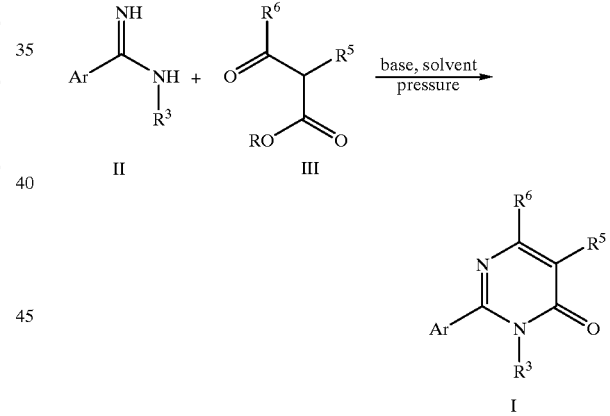

wherein

Ar is furyl, naphthyl, phenyl, pyridyl or thienyl; or furyl, naphthyl, phenyl, pyridyl or thienyl substituted with up to three substituents independently selected from bromo, chloro, fluoro, ($C_1$–$C_{12}$)alkyl, cyclo($C_3$–$C_8$) alkyl, ($C_2$–$C_{12}$)alkenyl, cyclo($C_3$–$C_8$)alkenyl, ($C_2$–$C_{12}$)alkynyl, halo($C_1$–$C_{12}$)alkyl, halo($C_2$–$C_{12}$) alkenyl, halo($C_2$–$C_{12}$)alkynyl, ($C_1$–$C_{12}$)alkoxy, ($C_1$–$C_{12}$)alkylthio, ($C_1$–$C_{12}$)alkylsulfonyl, ($C_1$–$C_{12}$) alkylsulfinyl, phenyl, phen($C_1$–$C_{12}$)alkyl, phen ($C_2$–$C_{12}$)alkenyl, phen($C_2$–$C_{12}$)alkynyl, cyano, halo ($C_1$–$C_{12}$)alkoxy, 1,3-dioxalan-2-yl and nitro; or furyl, naphthyl, phenyl, pyridyl or thienyl substituted on two adjacent carbon atoms by an alkylenedioxy to form a fused heterocyclic ring containing two oxygen atoms;

$R^3$ is ($C_1$–$C_6$)alkyl, ($C_3$–$C_6$)alkenyl, ($C_3$–$C_6$)alkynyl, ($C_1$–$C_6$)alkoxy($C_2$–$C_6$)alkyl, methyl or $C_3$ alkynyl substituted with up to three halo, or $(C_2-C_6)$alkyl, $(C_3-C_6)$ alkenyl, $(C_4-C_6)$alkynyl or $(C_1-C_6)$alkoxy$(C_2-C_6)$ alkyl all substituted with up to five halo;

$R^5$ is $(C_1-C_6)$alkyl, $(C_1-C_6)$alkoxy, halo$(C_1-C_6)$alkyl, halo$(C_1-C_6)$alkoxy or $(C_1-C_6)$alkylthio;

$R^6$ is $(C_1-C_{12})$alkyl or cyclo$(C_3-C_7)$alkyl; and

R is $(C_1-C_{12})$alkyl.

2. The process of claim 1 wherein

Ar is furyl, naphthyl, phenyl, 3,4-methylenedioxyphenyl, pyridyl, thienyl, or furyl, naphthyl, phenyl, pyridyl or thienyl substituted with up to three substituents independently selected from bromo, chloro, fluoro, $(C_1-C_6)$ alkyl, cyclo$(C_5-C_6)$alkyl, $(C_2-C_6)$alkenyl, cyclo$(C_5-C_6)$alkenyl, $(C_2-C_6)$alkynyl, halo$(C_1-C_6)$alkyl, halo$(C_2-C_6)$alkenyl, halo$(C_2-C_6)$alkynyl, $(C_1-C_6)$ alkoxy, $(C_1-C_6)$alkylthio, $(C_1-C_6)$alkylsulfonyl, $(C_1-C_6)$alkylsulfinyl, phenyl, phen$(C_1-C_6)$alkyl, phen$(C_2-C_6)$alkenyl, phen$(C_2-C_6)$alkynyl, cyano, halo $(C_1-C_6)$alkoxy, 1,3-dioxalan-2-yl and nitro;

$R^3$ is methyl, ethyl, n-propyl, $(C_3-C_4)$alkenyl, $(C_3-C_6)$ alk-2-ynyl, $(C_1-C_2)$alkoxy$(C_2-C_3)$alkyl, or methyl, ethyl, n-propyl, $(C_3-C_4)$alkenyl, $(C_3-C_6)$alk-2-ynyl, $(C_1-C_2)$alkoxy$(C_2-C_3)$alkyl substituted with one or more halo;

$R^5$ is methyl, ethyl, n-propyl, isopropyl, halo$(C_1-C_2)$ alkyl, halo$(C_1-C_2)$alkoxy, $(C_1-C_2)$alkoxy or $(C_1-C_2)$ alkylthio;

$R^6$ is methyl, ethyl, n-propyl, n-butyl, n-pentyl, n-hexyl, sec-butyl, isopropyl, isobutyl, cyclopropyl, cyclobutyl or cyclopentyl; and R is $(C_1-C_6)$alkyl.

3. The process of claim 2 wherein

Ar is 2-furyl, 3-furyl, 4-chloro-2-furyl, 5-chloro-2-furyl, 5-chloro-3-furyl, 2,5-dichloro-3-furyl, 2-naphthyl, phenyl, 3-methylphenyl, 3-methoxyphenyl, 3-nitrophenyl, 4-fluorophenyl, 4-chlorophenyl, 3-trifluoromethylphenyl, 3-bromophenyl, 3-chlorophenyl, 3-fluorophenyl, 3-trifluoromethoxyphenyl, 3-cyanophenyl, 3-(1,3-dioxolan-2-yl)phenyl, 2-fluorophenyl, 2-chlorophenyl, 2-trifluoromethoxyphenyl, 3,5-difluorophenyl, 3,5-dichlorophenyl, 2,4-difluorophenyl, 2,5-difluorophenyl, 3-chloro-4-fluorophenyl, 3,4-difluorophenyl, 3-fluoro-5-trifluoromethylphenyl, 3,4,5-trifluorophenyl, 3,4-methylenedioxyphenyl, 2-pyridyl, 4-chloro-2-pyridyl, 6-chloro-2-pyridyl, 4,6-dichloro-2-pyridyl, 3-pyridyl, 5-bromo-3-pyridyl, 5,6-dichloro-3-pyridyl, 5-chloro-3-pyridyl, 5-fluoro-3-pyridyl, 4-pyridyl, 2-fluoro-4-pyridyl, 2-chloro-4-pyridyl, 2-chloro-6-methyl-4-pyridyl, 2-methyl-4-pyridyl, 2-methoxy-4-pyridyl, 2-cyano-4-pyridyl, 2,6-difluoro-4-pyridyl, 2,6-dichloro-4-pyridyl, 2-thienyl, 3-thienyl, 4-chloro-2-thienyl, 5-chloro-2-thienyl, 5-chloro-3-thienyl or 2,5-dichloro-3-thienyl;

$R^3$ is ethyl, allyl, 3-chloroallyl, prop-2-ynyl, but-2-ynyl, pent-2-ynyl or 2-methoxyethyl;

$R^5$ is methyl, ethyl, halo$(C_1-C_2)$alkyl, difluoromethoxy, trifluoromethoxy, methoxy or methylthio;

$R^6$ is methyl, ethyl, n-propyl, sec-butyl, isopropyl, isobutyl, cyclopropyl, cyclobutyl or cyclopentyl; and R is $(C_1-C_4)$alkyl.

4. The process of claim 3 wherein

Ar is phenyl, 3-fluorophenyl, 3-chlorophenyl, 3,5-difluorophenyl, 3,5-dichlorophenyl, 3-chloro-4-fluorophenyl, 5-chloro-3-pyridyl, 2-chloro-4-pyridyl, 2,6-dichloro-4-pyridyl or 2-fluoro-4-pyridyl;

$R^3$ is prop-2-ynyl;

$R^5$ is methyl, ethyl or methoxy;

$R^6$ is methyl or ethyl, and

R is methyl or ethyl.

5. The process of claim 4 wherein Ar is phenyl or 2,6-dichloro-4-pyridyl.

6. The process of claim 1 wherein the reaction pressure is 6–20 Kbars.

7. The process of claim 6 wherein the reaction temperature is 0–100° C.

8. The process of claim 6 wherein the solvent is an alcohol.

9. The process of claim 8 wherein the alcohol is anhydrous methanol or ethanol.

10. The process of claim 6 wherein the base is a tertiary amine.

11. The process of claim 10 wherein the tertiary amine is triethylamine, diisopropylethylamine, pyridine or lutidine.

* * * * *